United States Patent [19]
Steinbruch et al.

[11] Patent Number: 6,156,505
[45] Date of Patent: Dec. 5, 2000

[54] **SPECIFIC DNA PROBES FOR THE IDENTIFICATION OF THE *TAENIA SOLIUM* AND *TAENIA SAGINATA* SPECIES**

[75] Inventors: Ana Flisser Steinbruch, Municipio de Huisquilucan, Mexico; Alger B. Chapman, Moss Beach; Nina M. Agabian, San Francisco, both of Calif.; Diana Maria Ortiz Garcia, Ecatepec; Veronica Vallejo Ruiz, Cholula, both of Mexico; Kevin G. Mossie, San Francisco, Calif.

[73] Assignees: Universidad Nacional Autonoma de Mexico, Distrito Federal, Mexico; The Regents of the University of California, Oakland, Calif.

[21] Appl. No.: 08/822,820

[22] Filed: Mar. 24, 1997

(Under 37 CFR 1.47)

Related U.S. Application Data

[60] Provisional application No. 60/005,186, Mar. 25, 1996.
[51] Int. Cl.$^7$ .............................. C12Q 1/68; C07H 21/02; C07H 21/04
[52] U.S. Cl. ........................... 435/6; 536/23.1; 536/24.32
[58] Field of Search ................................ 435/6; 536/23.1, 536/24.32

[56] References Cited

U.S. PATENT DOCUMENTS 4,740,456  4/1988  Kuhn et al. .................................. 435/7

OTHER PUBLICATIONS

Flisser, A. et al. Specific detection of *Taenia saginata* eggs by DNA hybridisation. Lancet 2:1429–1430, Dec. 1988.
Ahern, H. Biochemical, reagent kits offer scientists good return on investment. The Scientist 9(15):20, Jul. 1995.
Allan, J.C., et al., 1990, "Immunodiagnosis of Taeniasis by Coproantigen Detection," *Parasitology* 101: 473–7.
Allan, J.C., et al., 1992, Coproantigen detection for immunodiagnosis of echinococcosis and taeniasis in dogs and humans, *Parasitology* 104: 347–55.
Allan, J.C., et al., 1993, "Dipstick ELISA for the Detection of Taenia Coproantigens in Humans," *Parasitology* 107:79–85.
Bowles, J., et al., 1992, "Genetic Variants Within the Genus Echinococcus Identified by Mitochondrial DNA Sequencing," *Mol. Biochem. Parasitol.* 54:165–75.
Flisser, A., 1990, "New Approaches in the Diagnosis of *Taenia solium* cysticercosis and Taeniasis," *Ann. Parasitol. Hum. Comp.* 65:95–98.
Garey, J.R., and Wolstenholme, D.R., 1989, "Platyhelminth Mitochondrial DNA: Evidence for Early Evolutionary Origin of a tRNA (ser AGN) that Contains a Dihydrouridine Arm Replacement Loop," *J. Mol. Evol.* 28:374–8.
Harrison, L.J., et al., 1990, "Differential Diagnosis of *Taenia saginato* and *Taenia solium* with DNA Probes," *Parasitology* 100: 459–61.
Kinder, A., et al., 1992, "Salivary and Serum Antibodies in Experimental Canine Taeniasis," *Vet. Parasitol.* 41:321–7.

(List continued on next page.)

*Primary Examiner*—Carla J. Myers
*Assistant Examiner*—Diana Johannsen
*Attorney, Agent, or Firm*—Carol L. Francis; Paula A. Borden; Bozicevic, Field & Francis

[57] ABSTRACT

The invention features compositions and methods for the detection of and differentiation between *Taenia solium* and/or *Taenia saginata*. Specifically, the invention features nucleic acid probes comprising specific repetitive sequences of *T. solium* and *T. saginata*. These sequences make it possible to distinguish, with a high level of sensitivity and specificity, the eggs of these species of Taenia, thus enabling the diagnosis of taeniasis and the identification of carriers of *Taenia solium*. The invention is of great importance in controlling spread of *T. solium* due to ingestion of infected pork and/or exposure to human carriers of *T. solium*, thus facilitating the eradication of human and swine cysticercosis. The invention is thus of great importance in supporting eradication of human and swine cysticercosis.

13 Claims, 2 Drawing Sheets

OTHER PUBLICATIONS

McManus, D.P., et al., 1989, "Human Cysticercosis and Taeniasis: Molecular Approaches for Specific Diagnosis and Parasite Identification," *Acta Leiden* 57:81–91.

MacManus, D.P., et al., 1990, "Characterization of Taeniid Cestodes by DNA Analysis," *Rev. Sci. Tech. Off. Int. Epiz.* 9:489–510.

Pathak, K.M.L., et al., 1994, "A Western Blot and ELISA Assay for the Diagnosis of *Taenia solium* Infection in Pigs," *Vet. Parasitol.* 53:209–17.

Rishi, A.K. and MacManus, D.P., 1987, "DNA Probes which Unambiguously Distinguish *Taenia solium* from *T. saginata*," *Lancet* i:1275–76.

Rishi, A.K., and MacManus, D.P., 1988, "Molecular Cloning of *Taenia solium* genomic DNA and Characterization of Taeniid cestodes by DNA analysis," *Parasitology* 97:161–76.

Barker, D.C., "Molecular Approaches to DNA Diagnosis," *Parasitology*, 1989, vol. 99, pp. S125–S–146.

Chapman, et al., "Isolation and Characterization of Species–Specific DNA Probes form *Taenia Solium* and *Taenia Saginata* and Their Use in an Egg Detection Assay," *Journal of Clinical Microbiology.* May 1995, vol. 33(5), pp. 1238–1288.

Barker, D.C. Parasitology 99:S125–S146, 1989.

pTSol-9
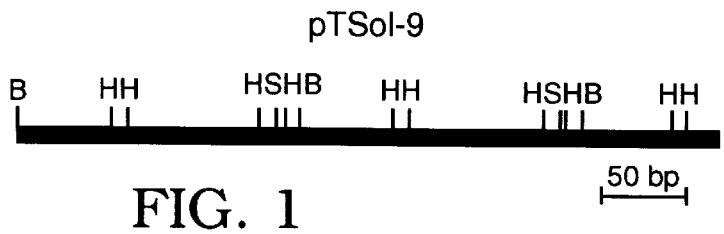
FIG. 1
```
          10          20          30          40          50
CAGGCAGGTG  CGCCACGTGG  CAGGGTGTGA  CGTCATGGCA  GGCAGCCTGG
          60          70          80          90         100
CCAATGGGCC  TGTCGGCGAT  CTGGGTCATG  TGCCGCAGTC  CACACGGCAA
         110         120         130         140         150
AGGACAGCCT  CCGAGGCGGT  TGCTAGGCAA  CTGGCCTCCT  CCCCGGGCCC
TGGGGATC
```
FIG. 2
pTSag-16
FIG. 3

```
           10         20         30         40         50
    CAAGCTCGCA CAGAAACACT GGTTTGTAAC CGAGAGATGC GGCTTCAGTG
           60         70         80         90        100
    CTATCGTGGA TGCCATGTCC TGGTGTTGTG TATGTGAATA CGGACGCTGT
          110        120        130        140        150
    CAAGATCGCC GTGTGTTTCC ATTACGTCCT GTCGATGGAA TAGCCACTTC
          160        170        180        190        200
    TTCCTTTTCC ACCTCTTCCT TCTCACCACT CCTGCTATGG GAGAATTGGA
          210        220        230        240        250
    CGTTTTTGAA CATCTTTATT ACAATCATAC GGAGGATGTG TGGTGGCGAA
          260        270        280        290        300
    ACCGAGACAG TTAAGACAAG GGTATCTCCG AGTCCGCAGA GCGATCACCA
          310        320        330        340        350
    ACACGAAATG GCATGCAGTG AGAGCGAAAT CTGCAGTGTG GTGAAGATCA
          360        370        380        390        400
    TAAGCGGGTT GGTATGATTT ATACTTTGTT GGGTTTGTGG TCAGGTTTTG
          410        420        430        440        450
    TAGGTTTAAG ATTTAGTTTA TTAATTCGTG TTAATTTTTT AGAGCCTTAT
          460        470        480        490        500
    TATAATGTGA TTTCTTTGGA TTGTTATAAT TTTTTGATTA CTAATCATGG
          510        520        530        540        550
    AATAATAATG ATTTTCTTTT TTTTAATGCC TATTTTAATA GGTGGTTTCG
          560        570        580        590        600
    GCAAATATTT AATTCCTTTG GTTGGTGGGT TATCTGATTT GAATTTACCC
          610        620        630        640        650
    CGTTTAAATG CTTTAAGTGC ATGGTTATTG ATTCCTTCGA TGGCTTTTCT
          660        670        680        690        700
    TTTGGTTAGT ATGTGTTTGG GTGCTGGTAT AGGGTGGACT TTTTATCCGC
          710        720        730        740        750
    CTTTGTCGTC ATCATTATTT TCAAGTAGTA ATGGTGTGGA TTTCTTGATG
          760        770        780        790        800
    TTTTCGTTGC ATTTGGCGGG TGCGTCTAGA ATTTTTAGTT CTATTAATTT
          810        820        830        840        850
    TATTTGTACT TTGTATAGAA TATTTATGAC TAATATATTT TCTCGTACTT
          860        870        880        890        900
    CTATAATATT GTGGGCTTAT TTATTTACGT CTATTTTATT ATTAGTTACT
          910        920        930        940        950
    CTTCCTGTAT TAGCAGCTGC TATCACTATG CTTTTATTTG ACCGTAAATT
          960
    TAGTTCTGCG TTTTTTG
```

FIG. 4

SPECIFIC DNA PROBES FOR THE IDENTIFICATION OF THE *TAENIA SOLIUM* AND *TAENIA SAGINATA* SPECIES

CROSS-REFERENCE TO RELATED APPLICATIONS

This application claims the benefit of priority under 35 U.S.C. §119(e) to provisional application Ser. No. 60/005,186, filed Mar. 25, 1996, which application is incorporated herein by reference.

STATEMENT AS TO RIGHTS TO INVENTIONS MADE UNDER FEDERALLY SPONSORED RESEARCH AND DEVELOPMENT

This invention was made with Government support under Grant No. AI00986 awarded by the National Institutes of Health and with partial support of contract CI1-0392 MEX from the European Community. The Government may have certain rights in this invention.

FIELD OF THE INVENTION

The invention is related generally to nucleic acid probes in detection of *T. solium* and *T. saginata* nucleic acid, especially nucleic acid contained within parasite eggs in a sample.

BACKGROUND OF THE INVENTION

The cestodes *Taenia solium* (pork tapeworm) and *Taenia saginata* (beef tapeworm) cause the two major forms intestinal taeniasis in humans (Pawlowski, Z. S., 1990, "Cestodiases: Taeniasis, Cysticercosis, Diphyllobothriasis, Hymenolepiasis, and Others," Tropical and Geographical Medicine (Warren, K. S., and Mahmoud, A. F., eds.) pp. 490–504, 2nd ed., McGraw Hill, New York). Both human and swine cysticercosis are acquired through ingestion of *T. solium* eggs. In contrast, ingestion of *T. saginata* eggs causes cysticercosis in cattle, but not in humans. Thus, the epidemiological importance of taeniasis produced by *T. solium* is not the same as that produced by *T. saginata*, since the former causes human cysticercosis, while the latter does not infect humans in it metacestode stage.

Cysticercosis caused by ingestion of *T. solium* eggs is a disease of particular importance in many developing countries (Flisser, A., 1988, Parasitol. Today, 4:131–137; Mahajan, R., 1982, "Geographic Distribution of Human Cysticercosis," Cysticercosis: Present State Knowledge and Perspectives (Flisser, A., et al., eds.), pp. 39–42, Academic Press, New York). Neurocysticercosis is the most common and serious form of cysticercosis in humans (Flisser, A., 1988, supra; Gemmell, M., et al., 1983, "Guidelines for Surveillance, Prevention and Control of taeniasis/cysticercosis," VPH/83.49, World Health Organization, Geneva, 1–207). Human cysticercosis is a serious problem for public health in developing countries, and implies heavy economic losses as a result of medical expenses, absenteeism and a gradual loss of the general state of health of the sick person. Furthermore, swine cysticercosis is a serious economic problem for pork production due to the confiscation of infected animals.

Cysticercosis was essentially eliminated from the developed countries at the beginning of the century by improving health infrastructure, health education and personal hygiene. Although this same approach would put an end to the present problem in underdeveloped countries, it is virtually impossible to apply these measures due to the high cost implied in the construction of suitable latrines in all the endemic regions, the low existing level of education and the difficulty of modifying habits and practices associated with food and health in communities where cysticercosis is endemic. Recently, cysticercosis has emerged again as a pathogen in some developed countries due to migration and tourism (Craig, P. S., et al., 1988, Trans. Royal Soc. Trop. Med. Hyg. 82:268–274; Earnest, M. P., et al., 1987, Rev. Infect. Dis., 9:961–979) further underscoring the need for control of this disease.

Cysticercosis normally results from ingestion of infected pork or from ingestion of other material contaminated with *T. solium* eggs. Because *T. solium* eggs are commonly shed by individuals harboring an adult tapeworm (Sarti, E. J., et al., 1988, Trop. Med. Parasitol. 39:194–198; Sarti, E., et al., 1992, Am. J. Trop. Med. and Hyg. 46:677–685; Schantz, P. M., et al., 1992, NEJM 327:692–695), control of this disease is largely dependent on reducing the contamination of water and food with *T. solium* eggs. In fact, recent epidemiological studies have shown that individuals with taeniasis are the principal risk factor for the propagation of cysticercosis (Sarti et al., 1994, Trans. Royal Soc. Trop. Med. Hyg. 88:49–52; Díaz-Camacho et al., 1991, Amer. J. Trop. Med. Hyg. 45:522–531).

Identification and treatment of human carriers of adult state tapeworms is a promising strategy to decrease the incidence of cysticercosis. However, identification of human carriers is complicated by the fact Taenia carriers are frequently asymptomatic (Faust, E. C., et al., 1970, Craig and Faust's Clinical Parasitology, pp. 502–507, 785–790, Lea and Febiger, Philadelphia; Gemmell, M., et al., 1983, supra; Pawlowski, Z. S., 1990, supra). Moreover, diagnosis of taeniasis is routinely performed by coproscopical examination (Faust, E. C., et al., 1970, supra), which has a low sensitivity of detection (Farahmandian, I., et al., 1973, Trop. Geogr. Med. 25:171–173). Because *T. solium* and *T. saginata* eggs have identical morphology (Faust, E. C., et al., 1970, supra, Gemmell, M., et al., 1983, supra), this method also does not allow the clinician to distinguish eggs of the Taenia species. While high sensitivity has been achieved with an ELISA for coproantigen detection of human Taenia carriers (Allan, J. C., et al., 1990, Parasitology 101:473–477), this assay cannot distinguish *T. solium* from *T. saginata* (Allan, J. C., et al., 1990, supra).

Diagnosis using repetitive DNA probes, which results in improved sensitivity, has been successful in *Trypanosoma cruzi* (Gonzalez, A., 1984, Proc. Natl. Acad. Sci. USA 81:3356–3360), Leishmania (Wirth, D. F., and Pratt, D. M., 1982, Proc. Natl. Acad. Sci. USA 79:6999–7003), *Plasmodium falciparum* (Barker, R. H., et al., 1986, Science 231:1434–1436), *Entamoeba histolytica* (Edman, U., et al., 1990, J. Exp. Med. 172:879–888; Garfinkel, L. I., et al., 1989, Infect. Immun. 57:926–931; Samuelson, J., et al., 1989, J. Clin. Microbiol. 27:671–676), and *Onchocerca vulvulus* (Erttmann, K. D., et al., 1987, Nature 327:415–417; Shah, J. S., et al., 1987, Am. J. Trop. Med. Hyg. 37:376–384) infections, among others. Most of these probes are repetitive sequences, resulting in highly sensitive hybridization assays. Moreover, the cost of these assays (US $0.17 per assay) is approximately half that of microscopic examination (Barker, R. H., et al., 1994, Int. J. Epidemio. 23:161–168).

Use of *T. solium* or *T. saginata* genomic DNA or species-specific taeniid DNA sequences to detect taeniid DNA has been described (McManus, 1990, Rev. Sci. Tech. Off. Int. Epiz. 9:489–510; McManus, D. P. et al., 1989, Acta Leiden 57:81–91; Harrison, L. J. et al., 1990, Parasitology 100:459–461; Flisser, A., 1990, Ann. Parasitol. Hum. Comp.

65:95–98; Rishi, A. K. and McManus, D. P., 1988, Parasitology 97:161–176; Rishi, A. K. and McManus, D. P., 1987, Lancet i:1275–1276). While the species-specific sequences can detect isolated taeniid DNA with at last some sensitivity and/or specificity, the sequences have either provided insufficient sensitivity or have not been tested for their ability to detect and distinguish *T. solium* and *T. saginata* eggs.

There is a need for compositions and methods that allow sensitive, rapid and noninvasive diagnosis that can differentiate the two species of Taenia, thereby allowing identification of *Taenia solium* carriers, who can then be treated.

SUMMARY OF THE INVENTION

The invention features compositions and methods for the detection of and differentiation between *Taenia solium* and/or *Taenia saginata*. Specifically, the invention features nucleic acid probes comprising specific repetitive sequences of *T. solium* and *T. saginata*. These sequences make it possible to distinguish, with a high level of sensitivity and specificity, the eggs of these species of Taenia, thus enabling the diagnosis of taeniasis and the identification of carriers of *Taenia solium*. The invention is of great importance in controlling spread of *T. solium* due to ingestion of infected pork and/or exposure to human carriers of *T. solium*, thus facilitating the eradication of human and swine cysticercosis.

The invention features specific nucleic acid probes useful for the identification of *Taenia solium* and *Taenia saginata*.

The invention also features methods for detecting *T. solium T. solium* using a *T. solium*-specific probe.

In one aspect, the method of the invention is used to detect *T. solium* in a human suspected of carrying *T. solium* by detecting eggs in a sample derived from the suspected carrier. In a preferred embodiment, the method is accomplished using both a species-specific *T. solium* nucleic acid probe and a *T. saginata* nucleic acid probe.

In another aspect, the invention is used to detect *T. solium* in swine suspected of carrying *T. solium*.

An advantage of the invention is that the probes can be used to create a highly sensitive and selective assay for the detection of *Taenia solium* and *Taenia saginata*.

Another advantage of the invention is that it can be carried out without the use of extensive laboratory equipment, thereby making it possible to carry out field tests.

Yet another advantage of the invention is that it allows early diagnosis and therefore early treatment of patients detected as being infected.

Still another advantage of the invention is that a *T. solium*-specific and/or *T. saginata*-specific nucleic acid probe(s) described herein can be combined with other methods for detection of *T. solium* and/or *T. saginata* to provide detection methods with improved sensitivity and specificity relative to those known in the art.

These and other objects, advantages and features of the present invention will become apparent those persons skilled in the art upon reading the details of the probes and assays and methods for using such as more fully set forth below.

BRIEF DESCRIPTION OF THE DRAWINGS

FIG. 1 is a restriction map of clone pTsol-9. Darkened segment indicates the position of a single 158 bp repeat unit. (S=SmaI, B=BamHI).

FIG. 2 is a schematic illustration of the DNA sequence of the first 158 bp repeat of *T. solium* (SEQ ID NO: 1).

FIG. 3 is a restriction map of clone pTsag-16. The open box contains sequences homologous to the mitochondrial cytochrome oxidase I gene (CO 1). (S=Sau3AI, E=EarI, H=HinfI, Ps=PstI, Pv=PvuII, X=XbaI).

FIG. 4 is a schematic illustration of the DNA sequence of the 967 bp clone (SEQ ID NO: 2).

DETAILED DESCRIPTION OF THE INVENTION

Before the present probes, assay devices and methods of using the probes and devices are described, it is to be understood that this invention is not limited to the particular probes, assays or methods as such may, of course, vary. It is also to be understood that the terminology used herein is for the purpose of describing particular embodiments only, and is not intended to be limiting since the scope of the present invention will be limited only by the appended claims. Unless defined otherwise, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are now described. All publications mentioned herein are incorporated herein by reference.

The publications discussed herein are provided solely for their disclosure prior to the filing date of the present application. Nothing herein is to be construed as an admission that the invention is not entitled to antedate such a disclosure by virtue of prior invention.

Definitions

The term "*Taenia solium*-specific nucleic acid probe" means a nucleic acid sequence of *T. solium* that binds, under selected hybridization conditions, *T. solium* genomic DNA with a sensitivity and specificity sufficient to facilitate detection of *T. solium* nucleic acid in a sample. Preferably, the *T. solium*-specific probe's binding sensitivity and specificity to *T. solium* nucleic acid is sufficient to facilitate detection of *T. solium* eggs in a sample, especially a sample that may additionally contain eggs and/or nucleic acid of other taenia species (e.g, *T. saginata, T. hydatigena, T. pisiformis,* and/or *T. taeniaeformis,* especially *T. saginata*), other eukaryotic parasites (e.g., *Echinococcus granulosus, Schistosoma mansoni, Caenorhabditis elegans, Entamoeba histolytica, Trypanosoma gambiense, Trypanosoma brucei,* and/or *Giardia lamblia*), other microorganisms such as fungi (e.g., *Saccharomyces cerevisiae, Candida albicans,* and/or *Cryptosporidium parvum*) or bacteria, and/or host nucleic acid sequences.

The term "*Taenia saginata*-specific nucleic acid probe" means a nucleic acid sequence of *T. saginata* that binds, under selected hybridization conditions, *T. saginata* genomic DNA with a sensitivity and specificity sufficient to facilitate detection of *T. saginata* nucleic acid in a sample. Preferably, the *T. saginata*-specific probe's binding sensitivity and specificity for *T. saginata* nucleic acid is sufficient to facilitate detection of *T. saginata* eggs in a sample, especially a sample that may additionally contain eggs and/or nucleic acid of other taenia species (e.g, *T. solium, T. hydatigena, T. pisiformis,* and/or *T. taeniaeformis,* especially *T. solium*), other eukaryotic parasites (e.g., *Echinococcus granulosus, Schistosoma mansoni, Caenorhabditis elegans, Entamoeba histolytica, Trypanosoma gambiense, Trypanosoma brucei,* and/or *Giardia lamblia*), other microorganisms such as fungi (e.g., *Saccharomyces cerevisiae, Candida*

*albicans,* and/or *Cryptosporidium parvum*) or bacteria, and/or host nucleic acid sequences.

The term "recombinant" or "genetically engineered" means a DNA sequence, or a polypeptide encoded thereby, generated using nucleic acid manipulation techniques (e.g., cloning, and/or PCR techniques). "Recombinant" or "genetically engineered" DNA, and thus the proteins encoded by such DNAs, do not occur in nature.

The term "sensitivity" means the conditional probability that the presence of a certain feature of a sample will be correctly detected by an experimental test (e.g., by nucleic acid probe binding to a target sequence). For diagnosis, sensitivity is defined as the conditional probability that a person having a disease will be correctly identified by a clinical test, i.e., the number of true positive results divided by the number of true positive and false negative results (Dorland's Illustrated Medical Dictionary, 28th Edition, W. B. Saunders Company, Philadelphia, Pa., 1994). For Southern blotting or other related hybridization techniques, the sensitivity of the assay is the conditional probability that the presence of a specific nucleotide sequence will be correctly identified during the blotting process.

The term "specificity" means the conditional probability that absence of a certain feature of a sample will be correctly identified by an experimental test. For diagnosis, specificity is defined as the conditional probability that a person not having a disease will be correctly identified by a clinical test, i.e., the number of true negative results divided by the number of true negative and false positive results (Dorland's Illustrated Medical Dictionary, 28th Edition, W. B. Saunders Company, Philadelphia, Pa., 1994). For Southern blotting or other related hybridization techniques, the specificity of the assay is the conditional probability that the absence of a specific nucleotide sequence will be correctly revealed during the blotting process.

The term "detectable label" means any molecule recognized in the art as a means for identifying and/or detecting a nucleic acid to which the detectable label is bound. Exemplary detectable labels include radionucleotides, fluorescent moieties, biotin, and antigenic molecules (e.g., which can be detected by binding of a detectably-labeled antibody).

The term "support" means any surface to which nucleic acid can be bound and immobilized. Preferably, the support is one that is suited to use in a hybridization assay (e.g., a dot blot assay). Exemplary supports include nitrocellulose and polymeric materials known in the art.

The term "subject suspected of carrying *Taenia solium*" means a human or member of the Suidae family, especially a domesticated member of the species *Sus scrofa* that is capable of being infected with *T. solium* and/or acting as a carrier for dissemination of *T. solium* eggs.

The term "subject suspected of carrying *Taenia saginata*" means a human, or member of the genus Bos (especially a domesticated member) that is capable of being infected with *T. saginata* and/or acting as a carrier for dissemination of *T. saginata* eggs.

The term "biological sample" as used herein in connection with detection of *T. solium* or *T. saginata* nucleic acid means a sample derived from or originating from a mammal suspected of carrying *T. solium* and/or *T. saginata*. Exemplary samples include, but are not necessarily limited to, clinical samples (e.g., stool or fecal samples, or biopsy samples), or samples from food products that may contain *T. solium* and/or *T. saginata* nucleic acid, especially *T. solium* and/or *T. saginata* eggs (e.g., food products containing pork or beef). In a preferred embodiment, the biological samples are suspected of containing *T. solium* and/or *T. saginata* eggs or cysts (e.g,. a stool or fecal sample).

The phrase "mammal suspected of having a *T. solium* infection" or "mammal suspected of having a *T. saginata* infection" is a mammal that is infected, either symptomatically (e.g,. presenting with symptoms of taeniasis or cysticercosis) or asymptomatically (e.g., having no detectable symptoms of taeniasis or cysticercosis), with *T. solium* or *T. saginata*, respectively. Mammals suspected of having a *T. solium* infection are generally limited to humans and swine, while mammals suspected of having a *T. saginata* infection are generally limited to humans and cattle. Asymptomatic mammals having a taeniid infection are generally referred to herein as "carriers."

Overview of the Invention

Cysticercosis results from the ingestion of the eggs of the tapeworm *Taenia solium*. Reduction of the incidence of human and swine cysticercosis requires identification and treatment of individuals who carry the adult tapeworm. *T. solium* and *T. saginata* eggs cannot be differentiated on the basis of morphology. To address this problem, the present invention provides highly-sensitive, species-specific nucleic acid probes that differentiate *T. solium* and *T. saginata*.

The *T. solium*-specific and *T. saginata*-specific probes were identified from genomic libraries of *T. solium* and *T. saginata* DNA, respectively by colony hybridization with labeled total genomic *T. solium* and *T. saginata* DNA. Recombinant clones from the genomic libraries that hybridized strongly were further screened for *T. solium*-specific or *T. saginata*-specific hybridization. *T. solium*-specific DNA sequences contained complete and truncated forms of a tandemly repeated 158 bp DNA sequence. An unrelated *T. saginata*-specific DNA sequence was also characterized and shown to encode a portion of the mitochondrial cytochrome c oxidase 1 (CO 1) gene.

The *T. solium*-specific and *T. saginata*-specific DNA probes did not hybridize in dot blot assays either with genomic DNA from the Platyhelminthes, *T. hydatigena, T. pisiformis, T. taeniaeformis, Echinococcus granulosus* and *Schistosoma mansoni* or with genomic DNA from other eukaryotes including *Saccharomyces cerevisiae, Candida albicans, Cryptosporidium parvum, Entamoeba histolytica, Trypanosoma gamiense, Trypanosoma brucei, Giardia lamblia, C. elegans* and human DNA.

The *T. solium*-specific and *T. saginata*-specific DNA probes are useful for rapid, highly-sensitive and specific detection of *T. solium* and/or *T. saginata* nucleic acid. The method of the invention using these probes involves collection of a sample suspected of containing *T. solium* and/or *T. saginata* nucleic acid, treating the sample to allow for binding of the probes to the *T. solium* and/or *T. saginata* nucleic acid, contacting the sample with a *T. solium*-specific and/or *T. saginata*-specific detectably-labeled probe, and detecting binding of the probe to the sample. In one embodiment of the method of the invention, the *T. solium* and/or *T. saginata* nucleic acid is present in the sample in the form of *T. solium* and/or *T. saginata* eggs. The various aspects of the invention will now be described in more detail.

Isolation of *T. solium* and *T. saginata* DNA probes

The detailed procedures for each of the steps followed in obtaining *T. solium*-specific and *T. saginata*-specific probes are outlined below.

DNA Purification

Methods for isolating DNA from parasites are known in the art. The method used to isolate parasite genomic DNA to obtain the probes of the present invention is outlined below.

1. A segment of a recently obtained tapeworm, or a segment that has been frozen or kept in 70% alcohol, is placed in a mortar which has been previously cooled with liquid nitrogen and is ground until a powder is obtained. The material is kept frozen during the whole process by adding liquid nitrogen.

2. The powder is immediately placed in a tube with a solution of DNA extraction (Tris, EDTA, SDS and proteinase K) and the suspension is incubated at 55° C. for 60 minutes.

3. DNA is extracted twice with a phenol-chloroform-isoamyl solution, and precipitated with 95% ethanol and highly concentrated salt at −20° C. for one hour, and is then harvested by centrifugation.

4. The DNA is suspended again in a buffer solution (Tris, EDTA), RNase A is added, and incubated at 37° C. for 30 minutes and the DNA is again extracted and precipitated.

Obtaining the Probes

Originally, DNA fragments were obtained from genomic libraries of *Taenia solium* and *Taenia saginata* for digestion with restriction enzymes, cloned into plasmid Bluescript KS (+/−) (registered trademark of Stratagene, protected under U.S. Pat. Nos. 5,128,256 and 5,286,356) and amplified in *Escherichia coli* XL-1. The colonies obtained were screened for specific repetitive sequences of *T. solium* and *T. saginata* by hybridization with total genomic DNA from both species. The clones that hybridized strongly with one of the DNAs were selected and characterized.

The production of the DNA probes can be accomplished using methods and compositions well known in the art (see, e.g., Sambrook et al., supra). For example, the nucleic acid probes inserted in the plasmid Bluescript KS (+/−) (registered trademark), and the probes amplified in *E. coli* using conventional protocols for plasmid extraction.

Characteristics of Nucleic Acid Probes of the Invention

The nucleic acid probes of the invention comprise a DNA or RNA, preferably DNA, sequence that binds to a nucleotide sequence (e.g., a genomic sequence) of either *T. solium* or *T. saginata* so as to facilitate detection of *T. solium* or *T. saginata* nucleic acid at a desired level of sensitivity and with a level of specificity sufficient to distinguish the presence of *T. solium* nucleic acid from the presence of *T. saginata* nucleic acid. Preferably, where the nucleic acid probe is *T. solium*-specific, the probe does not significantly bind to nucleic acid sequences of *T. saginata*; likewise, where the nucleic acid probe is *T. saginata*-specific, the probe does not significantly bind to nucleic acid sequence of *T. solium*. By "does not significantly bind" is meant that the level of probe binding is such that it is undetectable or can be readily distinguished from species-specific binding of the probe (e.g., a level of *T. solium*-specific probe binding to *T. saginata* DNA that is readily distinguishable from binding of the *T. solium*-specific probe to *T. solium* nucleic acid). The specificity of the species-specific probes may be affected by the conditions under which the probes are contacted with the target nucleic acid (e.g,. the stringency of the hybridization conditions). In a preferred embodiment the assay using the probes of the invention is performed under conditions that enhance the specificity of probe binding without significantly or substantially decreasing of the assay's sensitivity.

The probes can be used to detect *T. solium* or *T. saginata* nucleic acid in hybridization-based assays (e.g, Southern, Northern, dot blot, slot blot) or can be used as primers for assays using polymerase chain reaction (PCR). In a preferred embodiment, the probes are used in a dot blot assay where the sample (e.g., a nucleic acid sample or sample comprising taeniid eggs) is immobilized on a support. Preferably the sensitivity of the species-specific probe is such that the probe can facilitate species-specific detection of as little as about 200 ng to 500 ng *T. solium* or *T. saginata* nucleic acid, preferably as little as about 100 ng to 150 ng, more preferably about 50 ng to 75 ng, even more preferably as little as about 1 ng to 10 ngs of nucleic acid of *T. solium* or *T. saginata* in a sample. Where the probes are used to detect the presence of *T. solium* or *T. saginata* eggs in a sample, the probes and method of the invention can facilitate detection of as few as about 500 eggs to 1,000 eggs, preferably 100 eggs to 250 eggs, more preferably about 50 eggs to 75 eggs, still more preferably about 5 eggs to 10 eggs, most preferably as few as 1 egg in a sample.

*T. solium* Nucleic Acid Probes

The *T. solium* probes of the invention are derived from Sau3AI restriction fragments of *T. solium* genomic DNA and hybridize to a HaeIII restriction fragment of genomic *T. solium* DNA. The *T. solium* probes of the invention bind to *T. solium* nucleic acid so as to provide desired sensitivity and specificity, preferably such that the probe binds to *T. solium* nucleic acid at a level significantly or substantially greater than binding to *T. saginata* nucleic acid.

The *T. solium*-specific probe is preferably about 50 bp to about 800 bp in length, more preferably about 100 bp to about 500 bp in length, even more preferably about 150 bp to about 325 bp in length, most preferably about 158 bp in length. Preferably, the *T. solium* probes of the invention comprise at least one 158 bp repetitive sequence having the sequence of SEQ ID NO:1, and can comprises from 2 to 5 copies of the repetitive sequence or more. Alternatively, the *T. solium* probes of the invention comprise a fragment of the 158 bp repetitive sequence, or a sequence homologous to the 158 bp repetitive sequence, where the sequences is sufficient to detect *T. solium* nucleic acid with a desired sensitivity and specificity, preferably such that the probe binds to *T. solium* nucleic acid at a level significantly or substantially greater than binding to *T. saginata* nucleic acid.

Preferably, the specificity of the *T. solium*-specific probes of the invention is such that a detectably-labeled *T. solium*-specific probe binds to *T. solium* nucleic acid to provide a detectable signal that is at least 5 times to 10 times greater, preferably at least 50 times to 100 times greater, more preferably at least 1,000 times greater than the detectable signal associated with binding of the same detectably labeled *T. solium*-specific probe to *T. saginata* nucleic acid under the same binding conditions (e.g, hybridization stringency).

*T. saginata* Nucleic Acid Probes

The *T. saginata* probes of the invention are derived from Sau3AI restriction fragments of *T. saginata* genomic DNA. In one embodiment, the *T. saginata*-specific probe is preferably about 150 bp to 1750 bp in length, more preferably about 250 bp to 1100 bp in length, even more preferably about 300 bp to 700 bp in length, most preferably about 348 bp in length. In this first embodiment, the *T. saginata* probe comprises at least one 348 bp repetitive sequence having the sequence of nucleotides 1–347 of SEQ ID NO:2 (also referred to herein as a 5' repetitive sequence), and can comprises from 2 to 5 copies of the repetitive sequence or more. Alternatively, the *T. saginata* probe comprises a fragment of the 348 bp repetitive sequence, or a sequence homologous to the 348 bp sequence, that is sufficient to detect *T. saginata* nucleic acid with a desired sensitivity and specificity, preferably such that the probe binds to *T. saginata* nucleic acid at a level significantly or substantially greater than binding to *T. solium* nucleic acid.

In a second embodiment, the *T. saginata*-specific probe is preferably about 300 bp to 3,200 bp in length, more preferably about 400 bp to 2,500 bp in length, even more preferably about 300 bp to 1,300 bp in length, most preferably about 621 bp in length. In this second embodiment, the *T. saginata* probe comprises at least one 621 bp sequence having the sequence of nucleotides 348–967 of SEQ ID NO:2 (also referred to herein as the CO 1 homologous sequence), and can comprise from 2 to 5 copies of this sequence or more. Alternatively, the *T. saginata* probe comprises a fragment of the 621 bp sequence, or a sequence homologous to the 621 bp sequence, that is sufficient to detect *T. saginata* nucleic acid with a desired sensitivity and specificity, preferably such that the probe binds to *T. saginata* nucleic acid at a level significantly or substantially greater than binding to *T. solium* nucleic acid.

In another embodiment, the *T. saginata*-specific probe is composed of at least one 5' repetitive sequence (nucleotides 1–347 of SEQ ID NO:2) and at least one CO 1 homologous sequence (nucleotides 348–967 of SEQ ID NO:2). Preferably, the 5' repetitive sequence is adjacent and 5' of the CO 1 homologous sequence. The *T. saginata*-specific probe may comprise multiple copies (e.g., 2 to 5 copies or more) of the 5' repetitive sequence and/or multiple copies (e.g., 2 to 5 copies or more) of the CO 1 homologous sequence. Alternatively, the *T. saginata* probe can comprise fragments of the 5' repetitive sequence and/or CO 1 homologous sequence, and/or sequences homologous to the 5' repetitive sequence and/or CO 1 homologous sequence, that are sufficient to detect *T. saginata* nucleic acid with a desired sensitivity and specificity, preferably such that the probe binds to *T. saginata* nucleic acid at a level significantly or substantially greater than binding to *T. solium* nucleic acid.

Preferably, the specificity of the *T. saginata*-specific probes of the invention is such that a detectably-labeled *T. saginata*-specific probe binds to *T. saginata* nucleic acid to provide a detectable signal that is at least 5 times to 10 times greater, preferably at least 50 times to 100 times greater, more preferably at least 1,000 times greater than the detectable signal associated with binding of the same detectably labeled *T. saginata*-specific probe to *T. solium* nucleic acid under the same binding conditions (e.g, hybridization stringency).

Detectable Labels

The *T. solium*-specific and *T. saginata*-specific probes can be detectably labeled according to methods well known in the art. For example, the nucleic acid probes can be radioactively labeled (e.g., $^{35}S$ or $^{32}P$). Preferably, where the probe is to be used in the field to detect taeniid eggs in biological samples, the nucleic acid probes are labeled using a nonradioactive technique, e.g., fluorescein or biotin. The labeled probes can be detectably labeled DNA or RNA, preferably labeled DNA.

Detection of Taeniid Nucleic Acid in a Sample

The *T. solium*-specific and *T. saginata*-specific nucleic acid probes can be used to detect *T. solium* and/or *T. saginata* nucleic acid (e.g., DNA or RNA) according to a variety of techniques that are well known in the art (e.g, Southern hybridization, Northern hybridization, slot blot, dot blot, and other methods that involve binding of a labeled nucleic acid probe to a sample and detection of specific probe binding). The samples with which the probes of the invention can be used to detect *T. solium* and/or *T. saginata* nucleic acid can be any sample suspected of containing *T. solium* and/or *T. saginata*. For example, the sample can be a biological sample derived from a mammal suspected of having a *T. solium* and/or *T. saginata* infection (e.g., a fecal or stool sample, biopsy sample (e.g., tissue sample), or, where the mammal is a cow or pig, a sample derived from pork or beef, or products containing pork or beef). In a preferred embodiment, the sample comprises taeniid eggs, and the *T. solium*-specific and *T. saginata*-specific probes are used to detect the nucleic acid of eggs. Preferably, the samples are used in the assay of the invention immediately or soon after collection, or are stored in a manner to inhibit or prevent degradation of target DNA to be detected (e.g., storage in 70% ethanol).

Preferably, the assays are performed with negative and/or positive controls. For example, an appropriate negative control is a sample of DNA of a known concentration that does not hybridize to the *T. solium*-specific or *T. saginata* probe used in the assay (e.g., human genomic DNA). An appropriate positive control is, for example, a sample of DNA of a known concentration from the taeniid species corresponding to the probe used. In one embodiment, serial dilutions of the positive control DNA serves as means to quantitate the amount of *T. solium* or *T. saginata* DNA in the corresponding test sample. The amount of DNA in the test sample can then be correlated with for example, the number of eggs in the sample. Thus the assay of the invention can be performed either qualitatively or quantitatively.

The sensitivity and specificity of hybridization-based assays depends upon a number of factors including the amount of target DNA used, the proportion of the target sequence that is complementary to the probe, the size of the probe and its specific activity, the amount of target transferred to the filter, the stringency of the hybridization conditions, and the stringency of the washing solutions. Stringency is defined as the tolerance of the assay for mismatches between the probe and the target sequence of interest. When using oligonucleotide probes, the aim is to find conditions that are both stringent enough to guarantee specificity and sufficiently flexible to allow formation of stable hybrids at an acceptable rate. For a specific probe and target sequence, the stringency of the hybridization procedure can be altered by changing the temperature at which the reaction is carried out, the concentration of salt, and/or the amount of formamide in the hybridization buffer.

The $T_m$ is the calculated melting temperature of the hybrid formed between the probe and its target. For DNA molecules more than 200 nucleotides in length, hybridization is usually carried out at 15–25° C. below the $T_m$ of a perfect hybrid. It should be noted that as the length of the probe is decreased the $T_m$ is lowered to the point where it is often impractical to carry out hybridization at $T_m$-25° C., and thus hybridization for synthetic oligonucleotides is carried out under conditions that are only 5–10° C. below the $T_m$. Such stringent conditions reduce the number of mismatched clones that are detected with oligonucleotide probes, and they also reduce the rate at which the hybrids form. Methods and equations for calculating $T_m$ are well known in the art (see, e.g., Sambrook, J., et al., Molecular Cloning, A Laboratory Manual, Second Edition, Vol. 2, Cold Spring Harbor Laboratory Press, New York, 1989).

The stringency of washing following hybridization also affects the sensitivity and the specificity of hybridization-based assays. In general, the washing conditions used are as stringent as possible, so that a combination of temperature and salt concentration are chosen that is approximate 12–20° C. below the calculated $T_m$ of the hybrid under study.

The desired conditions for hybridization and washing can be readily determined empirically according to methods well known in the art. In general, for detection of moderate or high abundance sequences, hybridization is performed at 42° C. in a solution of 6 X SSC, and 50% formamide, with the addition of blocking agents, designed to inhibit nonspecific hybridization, such as 5X Denhardt's or 0.05 X BLOTTO. Standard washing conditions consist of washes in 2 X SSC and 0.5% SDS, followed by 2 X SSC and 0.1% SDS, followed by 0.1% SSC and 0.5% SDS. The stringency of the washing conditions can be changed by (1) altering the salt concentration, (2) altering the temperature, or (3) altering the concentration of SDS contained in the washing solution (see Sambrook, J., et al., supra).

Preferably, where the assay of the invention is based upon a hybridization technique, the hybridization is performed under conditions of stringency that provide for the desired sensitivity and specificity. Preferably, hybridization is performed under stringent conditions (e.g., performed at 42° C. overnight in 50% formamide, 6X SSC (1X SSC is 0.15 M NaCl, 0.015 M sodium citrate), 5X Denhardt's (5X Denhardt's is 0.1% Ficoll, 0.1% polyvinylpyrrolidone, 0.1% bovine serum albumin), and 10 µg/ml denatured salmon sperm DNA; then filters washed three times with 2X SSC, 0.1% SDS at 65° C., followed by 0.1X SSC, 0.1% SDS at 65° C.). The assay can be performed under conditions of lower or higher stringency (e.g., high stringency) if desired, providing the assay provides the desired sensitivity and specificity.

In an especially preferred embodiment, both the *T. solium*-specific and *T. saginata*-specific probes are used in parallel, thereby serving as an internal control. The *T. solium*-specific and *T. saginata*-specific probes can also be used in conjunction with other diagnostic methods (e.g., ELISA of coproantigens, assays with previously-described taeniid nucleic acid probes) to further increase the accuracy of the diagnosis.

Dot Blot Technique

In a preferred embodiment, the *T. solium*-specific and *T. saginata*-specific probes are used in a dot blot assay. The general steps of an exemplary dot blot assay are outlined below.

1. A membrane (e.g., Nytran, Zeta probe or nitrocellulose membranes) is dampened with distilled water and drops containing DNA (positive and negative control(s)) and different dilutions of the sample suspected of containing eggs are placed on the membrane. Where the assay is to be performed quantitatively, the control DNA is spotted onto the membrane in known amounts, which amounts can optionally be correlated to a number of eggs in a sample. Alternatively, samples containing known amounts of eggs can be spotted onto the membrane to facilitate quantitation of the eggs in the test samples. Prior to spotting on the membranes, the samples (both test and control) are treated to denature the DNA in the samples (e.g., by heating at 95° C. for 10 minutes in 4 volumes of denaturalizing solution), placed on ice, neutralized. Samples are placed directly onto the membranes using a pipette or by means of an apparatus in order to carry out the dot blot analysis.

2. The DNA is immobilized on the membrane (e.g., by subjecting the membranes to UV light), and hybridization is performed. The membranes can be hybridized with one of the detectably labeled *T. solium*-specific and *T. saginata*-specific probes. Alternatively, where the probes are differentially labeled (e.g., two different fluorescent probes that emit a detectable signal of sufficiently different wavelength), the membrane can be hybridized with the detectably labeled *T. solium*-specific and *T. saginata*-specific probes either concurrently or, preferably, consecutively (e.g., after washing away excess, unbound first probe).

3. The membranes are processed to detect the detectable signal bound to the probe(s). For example, where the probes are labeled with biotin, the membranes are processed with streptavidin. Alternatively, if the probes are labeled with fluorescein or digoxygenin, the membranes are processed with an antibody. Where the probes are labeled with an enzymatic system, one or more substrates can be used that dye the membranes (e.g, black, blue, green or red), thus making it possible to show the presence of *T. solium* or *T. saginata* eggs depending on the probe that has been used.

Detection of *T. solium* and/or *T. saginata* in Clinical Samples

In one embodiment, the probes of the invention are used to detect *T. solium* and/or *T. saginata* nucleic acid in a clinical sample (e.g., stool or fecal samples, or biopsy samples), especially clinical samples suspected of containing *T. solium* and/or *T. saginata* eggs. In a preferred embodiment, the biological samples are suspected of containing *T. solium* and/or *T. saginata* eggs or cysts (e.g,. a stool or fecal sample).

The probes of the invention can be used for direct detection of taeniid nucleic acid in the clinical sample (e.g, using dot blot analysis of a fecal sample dotted directly onto a membrane or, e.g., using PCR analysis directly with the sample). Alternatively, the clinical sample can be treated to at least partially purify the eggs from the samples according to methods well known in the art. Purification may be more desirable where the method of detection of the taeniid nucleic is PCR. The sample can be treated to release nucleic acid from the parasite eggs prior to detection (e.g., either with or without partial purification of the eggs from the sample). Preferably, the method employed for detecting the taeniid nucleic acid in the sample is a relatively simple method that can be readily adapted to field and/or clinic use. It may also be desirable to process the samples using an automated process, particularly where the assay is performed in a clinic setting or in a commercial laboratory.

The assay can be optimized according to methods well known in the art. Preferably, a clinical assay according to the invention utilizes a nonradioactive detection reagent that does not require special equipment, thereby facilitating use in epidemiological studies under field conditions. As shown in the case of *Plasmodium falciparum* diagnosis, DNA probe hybridization procedures can be performed on clinical specimens in laboratories of both developed and developing countries with similar results (Barker, R. H., et al., 1994, Int. J. Epidemio. 23:161–168). The cost of these assays (US $0.17 per assay) was approximately half that of microscopic examination.

The primary aim of the clinical assays of the invention is the detection of *T. solium* eggs, and distinguishing infections with *T. solium* eggs from infections with *T. saginata* eggs, in the control of neurocysticercosis. One focus of such neurocysticercosis control campaigns aim to detect and treat *T.*

*solium* tapeworm carriers, and avoid unnecessary treatment of carriers of *T. saginata*. The assay of the invention is also useful in nonendemic areas in screening immigrants for *T. solium* tapeworm carriage in order to prevent the kind of locally acquired neurocysticercosis recently found in New York City (Schantz, P. M., et al., 1992, supra).

Detection of *T. solium* and/or *T. saginata* Eggs in Food Products

The probes and methods of the invention can also be used to detect *T. solium* and/or *T. saginata* nucleic acid in livestock and/or samples from food products that may contain *T. solium* and/or *T. saginata* nucleic acid, (e.g., food products containing pork or beef). Because the parasites are located within the muscle of an infected pig or cow, detection of a *T. solium* or *T. saginata* infection, respectively, can be accomplished by 0detecting nucleic acid of the parasite in a muscle sample that has been processed as needed to make the taeniid nucleic acid available to the probe (e.g., by grinding the biopsy sample). Alternatively, the taeniid nucleic acid may be detected in a blood sample from the animal suspected of having a parasitic infection. Where the sample is a blood sample, preferably the taeniid nucleic acid is detected using PCR.

Where the sample is from a food product suspected of having *T. solium* and/or *T. saginata*, the probes of the invention can be used in a direct dot blot assay of the food product sample, or can be subjected to PCR using the probes of the invention. Alternatively, the sample can be treated to at least partially purify the parastie and/or the taeniid nucleic acid from the samples according to methods well known in the art. Purification may be more desirable where the method of detection of the taeniid nucleic is PCR. The sample can be treated to release nucleic acid from the parasites prior to detection (e.g., either with or without partial purification of the sample). Preferably, the method employed for detecting the taeniid nucleic acid in the sample is a relatively simple method that can be readily adapted to use in food processing plants or at other appropriate sites where quality control is implemented. It may also be desirable to process the samples using an automated process, particularly where the assay is performed in a commercial laboratory.

Utility

The DNA probes described in this invention have proved to be of value in identifying *T. solium* eggs and distinguishing them from those of *T. saginata*. This invention can therefore be used in the diagnosis of taeniasis in clinical laboratories as part of their routine work. Not only can the invention distinguish the two species of Taenia species, but it also considerably improves (by about 50%) diagnostic sensitivity. At present the diagnosis of taeniasis is carried out in clinical analysis laboratories through the coproparasitoscopic technique, which has a low degree of sensitivity, cannot distinguish the Taenia species and requires the technician to have considerable skill with respect to the use of a microscope.

Furthermore, the present invention is of considerable importance for countries in which human cysticercosis is a public health problem. Use of the probes and detection/diagnostic methods of the invention make it possible to carry out a taeniasis diagnosis in the field. This is highly significant in epidemiological studies for the control of human and swine cysticercosis, since diagnosis in situ of the carriers of taeniasis means that they can be treated immediately to eliminate the parasite and thus avoid individually contaminating the environment and continuing to be a source of infection of cysticercosis for other human beings and for pigs. Because the method of the invention can differentiate between *T. solium* and *T. saginata*, clinicians can avoid treating subjects infected with *T. saginata*, which is of less importance epidemiologically, thereby saving the expense of needless treatment.

EXAMPLES

The following examples are put forth so as to provide those of ordinary skill in the art with a complete disclosure and description of how to carry out the invention and is not intended to limit the scope of what the inventors regard as their invention. Efforts have been made to ensure accuracy with respect to numbers used (e.g., amounts, temperatures, etc.), but some experimental error and deviation should be accounted for. Unless indicated otherwise, parts are parts by weight, molecular weight is weight average molecular weight, temperature is in degrees Centigrade, and pressure is at or near atmospheric pressure.

Example 1

Construction and Screening of *T. solium* and *T. saginata* Genomic Libraries

*T. solium* cysticerci were obtained from the carcass of a naturally infected pig, immediately frozen and stored at −20° C. An adult *T. saginata* worm was obtained from a patient and stored in 70% ethanol. Several gravid proglottids from two adult *T. solium* obtained in China in 1988 and from two worms collected in Mexico in 1992 were kept in 70% ethanol.

Parasite DNA was prepared using a modification of the protocol described by Sambrook et al. (Sambrook, J., et al., 1989, Molecular Cloning: A Laboratory Manual, 2nd ed., Cold Spring Harbor, N.Y.). Briefly, frozen parasites were placed in a mortar precooled and partially filled with liquid nitrogen and ground to a fine powder with a chilled pestle. The powder was suspended in DNA extraction buffer (50 mM Tris.HCl pH 7.5, 50 mM EDTA pH 8.0, 0.5% SDS w/v, 200 μg/ml proteinase K) and incubated at 55° C. for 60 min. DNA was extracted twice with an equal volume of phenol: chloroform: isoamyl alcohol (25:24:1). Nucleic acids were precipitated with 95% ethanol and high salt at −20° C. for 1 hr and harvested by centrifugation at 10,000 rpm. The pellet was suspended in TE buffer (10 mM Tris.HCl pH 7.5, 1 mM EDTA), RNase A was added to 20 μg/ml final concentration and incubated at 37° C. for 30 min. The reaction mixture was then extracted and ethanol precipitated as described above.

Genomic DNA from *T. solium* or *T. saginata* was partially restricted with Sau3AI to yield fragments ranging from 300 bp to approximately 5 kb. The fragments were cloned into the BamHI site of pBluescript KS (+/−) (Stratagene, La Jolla, Calif., USA) and amplified in the *E. coli* host XL-1. *T. solium* and *T. saginata* plasmid libraries of $2.8 \times 10^7$ and $3.9 \times 10^7$ recombinant clones respectively each contained insert of 0.3 kb to >7 kb.

Approximately 3000 colonies from each library were screened for repetitive sequences by colony hybridization (Grunstein and Hogness, 1975, Proc. Natl. Acad. Sci. USA 72:3961–3965) with total genomic *T. solium* or *T. saginata* DNA which had been $^{32}$P-labeled by random primer extension (Sambrook, J., et al., 1989, supra). Those recombinant clones which hybridized strongly with the probe were chosen for further characterization.

Example 2

Isolation and Characterization of *T. solium* Recombinant Clones

Forty recombinant clones that hybridized strongly with the labeled *T. solium* genomic DNA in Example 1 were isolated from the *T. solium* genomic library and used as probes in Southern analysis to assay for species-specific hybridization. $^{32}$P-labeled plasmid DNA probes were prepared from the *T. solium* recombinant clones using random hexamer primers (Sambrook, J., et al., 1989, supra), and used for Southern analysis of Taenia genomic DNAs. Genomic DNA prepared from *T. solium, T. saginata, T. hydatigena, T. pisiformis,* and *T. taeniaeformis* was digested with several endonucleases. A 5 µg sample of the genomic restricted DNA from each different taeniid species was subjected to electrophoresis in 1.0% agarose gels, and immobilized on either nitrocellulose or Nytran filters (Schleicher & Schuell, Keene, N.H.) (Southern, E. M., 1975, J. Mol. Biol. 98:503–517) as recommended by the manufacturer. Hybridizations were performed at 42° C. overnight in 50% formamide, 6X SSC (1X SSC is 0.15 M NaCl, 0.015 M Sodium citrate), 5X Denhardt's (5X Denhardt's is 0.1% Ficoll, 0.1% polyvinylpyrrolidone, 0.1% bovine serum albumin), and 10 µg/ml denatured salmon sperm DNA. Filters were washed three times with 2X SSC, 0.1% SDS at 65° C., followed by 0.1X SSC, 0.1% SDS at 65° C. Hybridization of labeled probed was visualized by autoradiography.

Clones showing species-specific hybridization were selected for further analysis and DNA sequencing. Recombinant clones were sequenced using chain terminators and an automated sequencing protocol (Applied Biosystems) (Sanger, F., et al., 1977, Proc. Natl. Acad. Sci. USA 74:5463–5467). Sequence comparisons were done using the Pearson and Lipman method (Pearson, W. R., and Lipman, D. J., 1988, Proc Natl Acad Sci 85:2444–2448) and the GenBank database.

Approximately half of the *T. solium* clones hybridized equally well with genomic DNA from both *T. sodium* and *T. saginata*; these were not investigated further. The remaining clones from the *T. solium* library hybridized predominantly with *T. solium* DNA. As determined by Southern blotting, many of these clones hybridized to the same small *T. solium* DNA band generated after Hae III digestion, suggesting that these clones contain a common repeated DNA sequence.

One of these clones, pTsol-9, was chosen for further analysis. To confirm that many of the *T. solium* specific recombinant clones contained the same repetitive sequence, we used the pTsol-9 insert as a hybridization probe against Southern blot filters containing all recombinant clones. As expected, many inserts from recombinant clones (11/31; approximately 30%) hybridized to the pTsol-9 probe, suggesting that the sequence contained within the approximately 400 bp pTsol-9 insert was represented frequently in the *T. solium* genome. Structural analysis of some of the pTsol-hybridizing recombinant clones indicated that this repetitive sequence is tandemly arranged and contains Hae III fragments of 76, 61 and 8 bp which superimpose as a single prominent band in Southern blots.

The specificity of pTsol-9 probe was assayed by Southern blot hybridization to DNA from other taeniid species. The presence of a single predominant hybridizing band in the Hae III digested *T. solium* genomic DNA lane suggested that this repeat uniformly contained Hae III restriction sites. In addition to the prominent hybridization to *T. solium* DNA, faint hybridization was detected in restriction digests containing *T. saginata* DNA. This slight cross-hybridization of the pTsol-9 probe with *T. saginata* genomic DNA may be nonspecific, due to a low copy number of the repeat in the heterologous DNA or due to the presence of a structurally similar but divergent sequence. Diagnostics based upon the pTsol-9 probe may thus preferably include use of negative and positive controls containing *T. saginata* and *T. solium* DNA, respectively, and/or use of a *T. saginata*-specific probe in parallel. No hybridization of the pTsol-9 probe was detected in the samples containing *T. hydatigena, T. pisiformis* or *T. taeniaeformis* DNA.

Restriction mapping of pTsol-9 confirmed the presence of a repeat structure (FIG. 1). The repeat has 158 bp and is tandemly organized with four Hae III sites and a single Bam HI site per repeat unit. The nucleotide sequence of a pTsol-9 repeat (SEQ ID NO:1) is shown in FIG. 2.

Example 3

Isolation and Characterization of *T. saginata* Recombinant Clone

Forty recombinant clones that hybridized strongly with labeled *T. saginata* genomic DNA in Example 1 were isolated from the *T. saginata* genomic library and used as probes in Southern analysis to assay for species-specific hybridization to *T. saginata* DNA as described in Example 2. One clone, pTsag-16, with an insert size of 967 bp, contained a repetitive sequence that was specific for *T. saginata* as determined by Southern blot analysis; there was very little cross-hybridization to *T. solium* DNA. The pTsag-16 clone was sequenced as described in Example 2. The restriction map and nucleotide sequence of pTsag-16 (SEQ ID NO:2) are shown in FIGS. 3 and 4, respectively. Surprisingly, when the sequence was used to search the GenBank database using the Pearson and Lipman method (Pearson, W. R., and Lipman, D. J., 1988, supra), extensive homology was found in a 629 bp Sau3AI fragment to the mitochondrial gene cytochrome c oxidase I (CO 1), including up to 70% identity in both nucleotide and amino acid sequences with the platyhelminth *Fasciola hepatica* (Garey, J. R., and Wolstenholme, D. R., 1989, J. Mol. Evol. 28:374–378). This region of homology is flanked by 347 bp which show no homology to the CO 1 gene, suggesting that the pTsag-16 clone contains two separate inserts, a mitochondrial CO 1 gene fragment (bp 347–967), and a repeated DNA fragment (bp 1–346) ligated at their Sau3AI ends during the generation of the *T. saginata* genomic library. This hypothesis was confirmed by the absence in Southern blots of a predicted 350 bp HinII fragment spanning this Sau3AI site. Although sequences from a region of the CO 1 gene have been reported for the cestode Echinococcus (Bowles, J., et al., 1992, Mol. Biochem. Parasitol. 54:165–174), which is more closely related to *T. saginata* than is *Fasciola hepatica*, no direct comparisons to our reported *T. saginata* CO 1 gene fragment could be made since our sequence derives from a different region of the CO 1 gene.

These two unrelated inserts, the CO 1 fragment (621 bp fragment of pTsag-16) or the 5'pTsag-16 fragment (348 bp XbaI-PstI fragment of pTsag-16), were isolated and used as probes for Southern analysis of genomic restricted DNA from *T. solium* and *T. saginata* according to the method described above.

With such extensive homology of the *T. saginata* CO 1 gene to that of Fasciola hepatica, which belongs to a different class of platyhelminths, one might expect even greater homology to another cestode such as *T. solium*. This expected homology may explain the faint signals that were detected in *T. solium* DNA by pTsag-16; although when probed separately, both fragments (bp 1–346 and bp 347–997) yielded minimal cross-reactivity to *T. solium* DNA.

Despite the strong evolutionary conservation of the CO 1 mitochondrial gene, when the *T. saginata* CO 1 gene fragment and the 5' repetitive DNA fragment were hybridized separately against *T. saginata* and *T. solium* genomic DNA, both fragments showed a high degree of specificity for *T. saginata* DNA with minimal cross-hybridization to *T. solium* DNA. The approximately 16 kb CO 1 signal in the Hae III digests represented a significant fraction of the total pTsag-16 signal detected in the Southern analysis of Example 3. This 16 kb CO 1 band is likely to represent mitochondrial DNA monomers. While the CO 1 gene is probably a single copy mitochondrial gene, its intensity on a Southern blot might be expected to approach that seen with the 346 bp repetitive sequence depending on the average number of mitochondria per cell.

Example 4

Specificity of pTsol-9 and pTsag-16 in Dot Blots

The specificity of pTsol-9 and pTsag-16 was examined using dot blot analysis. Preheated (95° C.) genomic DNA from *T. hydatigena, T. pisiformis, T. taeniaeformis, Echinococcus granulosus, Schistosoma mansoni, Caenorhabditis elegans, Entamoeba histolytica, Trypanosoma gambiense, Trypanosoma brucei, Giardia lamblia, Saccharomyces cerevisiae, Candida albicans, Cryptosporidium parvum* and *Homo sapiens* DNA was serially diluted and spotted onto Nytran filters to provide samples containing approximately 50 ng, 100 ng, 150 ng, and 200 ng. The filters were baked and hybridized with the species-specific pTsol-9 and pTsag-16 probes as described above. Approximately 25 ng of each of the labeled pTsol-9 and pTsag-16 plasmids were used.

pTsol-9 hybridizing sequences are much more abundant in the *T. solium* genome than in *T. saginata*. The pTsol-9 probe provided a strong signal easily detectable at even the lowest concentration of *T. solium* DNA tested. In contrast, pTsol-9 probe hybridization to *T. saginata* DNA resulted in a weak signal, and only at the highest DNA concentration tested (200 ng).

Conversely, the pTsag-16 insert was more abundant in the *T. saginata* genome than in *T. solium*. The pTsag-16 probe provided a strong signal with 100 ng *T. saginata* DNA. However, pTsag-16 probe hybridization to *T. solium* DNA resulted in only a barely detectable signal even at the highest DNA concentration tested (200 ng).

Dot blot analysis was also performed on DNAs from several eukaryotic pathogens which are coendemic with Taenia in some regions and thus might confound diagnostic assays. pTsol-9 did not hybridize to purified genomic DNA from *E. histolytica, E. granulosus, S. mansoni, C. elegans, T. brucei, T. gambiense, G. lamblia, S. cerevisiae, C. albicans, Cryptosporidium parvum* and *Homo sapiens*. The pTsag-16 probe did show some faint hybridization with *E. granulosus* at the highest concentration of DNA tested (200 ng).

Example 5

Sensitivity and Specificity of the Recombinant Probes on Purified *Taenia solium* Eggs The specificity and sensitivity of the recombinant probes for diagnostic purposes was analyzed in dot blots of serial dilutions of purified *T. solium* eggs isolated from gravid segments as described previously (Flisser, A., et al., 1988, Lancet, December 17, 1429–1430). Four different *T. solium* egg samples were tested: two samples were taken from eggs obtained in China and kept in 70% ethanol since 1988; two samples were from eggs obtained in Mexico in 1992 and kept in 70% ethanol. One of the Mexican samples was not well preserved.

Conditions used for denaturation of purified eggs were determined empirically and consisted of adding 4 volumes of 0.2N NaOH and boiling for 10 min. The eggs were then chilled in ice, neutralized and dotted (immobilized) in different amounts (samples corresponding to 1 egg, 5 eggs, 10 eggs, 50 eggs, 100 eggs, and 500 eggs) on a Zetta-probe membrane (Bio-Rad, Richmond, Calif.). As a control, 1 ng of *T. solium* DNA, pTsol-9, pTsag-16 and *T. saginata* DNA were also dotted onto the membranes. The membranes were then hybridized with $^{32}P$ labeled pTsol-9 or pTsag-16 probes as described above.

The assay demonstrated remarkable sensitivity with as little as one *T. solium* egg detected by the pTsol-9 probe. Specificity was also high since no cross-hybridization with pTsag-16 occurred. Hybridization was less sensitive when using eggs obtained in China that had been stored for several years; no signal was detected using eggs obtained recently in Mexico from a proglottid that was not properly preserved.

The dot blot analysis of *T. solium* eggs demonstrates that the pTsol-9 and pTsag-16 repetitive sequences when used alone or, perhaps preferably in some instances, in conjunction can provide a specific and sensitive DNA probes for the detection of *T. solium* eggs. The dot blot analysis suggests that there is some deterioration in signal over time. Eggs isolated from the Chinese samples were the same ones that were used several years ago to standardize a DNA hybridization assay in Flisser, A., et al., 1988, supra; when used at that time even one egg could be detected, while now 50 or more are needed.

The invention now being fully described, it will be apparent to one of ordinary skill in the art that many changes and modifications can be made thereto without departing from the spirit or scope of the appended claims.

What is claimed is:

1. A nucleic acid probe for detection of *Taenia solium* nucleic acid in a sample, wherein said probe hybridizes to nucleic acid of *Taenia solium* eggs at a level sufficient to distinguish nucleic acid of *Taenia solium* eggs from nucleic acid of *Taenia saginata* eggs, and wherein said probe is selected from the group consisting of:
   a) a probe consisting of the repetitive sequence of SEQ ID NO: 1 or from 2 to 5 copies of the repetitive sequence of SEQ ID NO: 1;
   b) a probe consisting of an approximately 400 base pair Sau3A1 fragment obtained by restriction digestion of *Taenia solium* genomic DNA or a *Taenia solium* genomic DNA library, wherein said fragment comprises SEQ ID NO: 1;
   c) a probe consisting of a subfragment of the approximately 400 base pair Sau3A1 fragment of b), wherein said subfragment comprises SEQ ID NO: 1; and d) a vector comprising an insert consisting of a probe selected from the group of a), b), and c).

2. The probe of claim 1, wherein the probe hybridizes to nucleic acid of *Taenia solium* eggs under stringent conditions.

3. A nucleic acid probe selected from the group consisting of:
   a) a probe consisting of the repetitive sequence of SEQ ID NO: 1 or from 2 to 5 copies of the repetitive sequence of SEQ ID NO: 1;
   b) a probe consisting of an approximately 400 base pair Sau3A1 fragment obtained by restriction digestion of *Taenia solium* genomic DNA or a *Taenia solium* genomic DNA library, wherein said fragment comprises SEQ ID NO: 1;
   c) a probe consisting of a subfragment of the approximately 400 base pair Sau3A1 fragment of b), wherein said subfragment comprises SEQ ID NO: 1; and d) a vector comprising an insert consisting of a probe selected from the group of a), b), and c).

4. A nucleic acid probe for detection of *Taenia saginata* nucleic acid in a sample, wherein said probe hybridizes to nucleic acid of *Taenia saginata* eggs at a level sufficient to distinguish nucleic acid of *Taenia saginata* eggs from nucleic acid of *Taenia solium* eggs, and wherein said probe is selected from the group consisting of:

a) a probe consisting of nucleotides 1–347 of SEQ ID NO: 2, from 2 to 5 copies of nucleotides 1–347 of SEQ ID NO: 2, nucleotides 348–967 of SEQ ID NO: 2, or from 2 to 5 copies of nucleotides 348–967 of SEQ ID NO: 2;

b) a probe consisting of SEQ ID NO: 2;

c) a probe consisting of a fragment of SEQ ID NO: 2, wherein said fragment comprises at least nucleotides 1–347 of SEQ ID NO: 2 or nucleotides 348–967 of SEQ ID NO: 2; and d) a vector comprising an insert consisting of a probe selected from the group of a), b), and c).

5. The probe of claim 4, wherein the probe hybridizes to *Taenia saginata* eggs under stringent conditions.

6. A method for detecting *Taenia solium* eggs in a sample, the method comprising the steps of:

contacting a test sample suspected of comprising *Taenia solium* eggs with a detectably labeled nucleic acid probe, wherein said probe hybridizes to nucleic acid of *Taenia solium* eggs at a level sufficient to distinguish nucleic acid of *Taenia solium* eggs from nucleic acid of *Taenia saginata* eggs, and wherein said probe is selected from the group consisting of:

a) a probe consisting of the repetitive sequence of SEQ ID NO: 1 or from 2 to 5 copies of the repetitive sequence of SEQ ID NO: 1;

b) a probe consisting of an approximately 400 base pair Sau3A1 fragment obtained by restriction digestion of *Taenia solium* genomic DNA or a *Taenia solium* genomic DNA library, wherein said fragment comprises SEQ ID NO: 1;

c) a probe consisting of a subfragment of the approximately 400 base pair Sau3A1 fragment of b), wherein said subfragment comprises SEQ ID NO: 1; and d) a vector comprising an insert consisting of a probe selected from the group of a), b), and c); and detecting nucleic acid probe bound to the test sample;

wherein an amount of probe bound to the test sample higher than an amount of probe bound to a negative control sample is indicative of the presence of *Taenia solium* eggs in the sample.

7. The method of claim 6, wherein the test sample is a biological sample.

8. The method of claim 7, wherein the biological sample is from a human.

9. The method of claim 7, wherein the biological sample is from a pig.

10. The method of claim 6, wherein the sample is a sample of a pork-containing food product.

11. A kit for detecting *Taenia solium*, the kit comprising a container containing a nucleic acid probe selected from the group consisting of:

a) a probe consisting of the repetitive sequence of SEQ ID NO: 1 or from 2 to 5 copies of the repetitive sequence of SEQ ID NO: 1;

b) a probe consisting of an approximately 400 base pair Sau3A1 fragment obtained by restriction digestion of *Taenia solium* genomic DNA or a *Taenia solium* genomic DNA library, wherein said fragment comprises SEQ ID NO: 1;

c) a probe consisting of a subfragment of the approximately 400 base pair Sau3A1 fragment of b), wherein said subfragment comprises SEQ ID NO: 1; and d) a vector comprising an insert consisting of a probe selected from the group of a), b), and c).

12. A kit for detecting *Taenia saginata*, the kit comprising a container containing a nucleic acid probe selected from the group consisting of:

a) a probe consisting of nucleotides 1–347 of SEQ ID NO: 2, from 2 to 5 copies of nucleotides 1–347 of SEQ ID NO: 2, nucleotides 348–967 of SEQ ID NO: 2, or from 2 to 5 copies of nucleotides 348–967 of SEQ ID NO: 2;

b) a probe consisting of SEQ ID NO: 2;

c) a probe consisting of a fragment of SEQ ID NO: 2, wherein said fragment comprises at least nucleotides 1–347 of SEQ ID NO: 2 or nucleotides 348–967 of SEQ ID NO: 2; and d) a vector comprising an insert consisting of a probe selected from the group of a), b), and c).

13. A method for detecting *Taenia saginata* eggs in a sample, the method comprising the steps of:

contacting a test sample suspected of comprising *Taenia saginata* eggs with a detectably labeled nucleic acid probe, wherein said probe hybridizes to nucleic acid of *Taenia saginata* eggs at a level sufficient to distinguish nucleic acid of *Taenia saginata* eggs from nucleic acid of *Taenia solium* eggs, and wherein said probe is selected from the group consisting of:

a) a probe consisting of nucleotides 1–347 of SEQ ID NO: 2, from 2 to 5 copies of nucleotides 1–347 of SEQ ID NO: 2, nucleotides 348–967 of SEQ ID NO: 2, or from 2 to 5 copies of nucleotides 348–967 of SEQ ID NO: 2;

b) a probe consisting of SEQ ID NO: 2;

c) a probe consisting of a fragment of SEQ ID NO: 2, wherein said fragment comprises at least nucleotides 1–347 of SEQ ID NO: 2 or nucleotides 348–967 of SEQ ID NO: 2; and d) a vector comprising an insert consisting of a probe selected from the group of a), b), and c); and detecting nucleic acid probe bound to the test sample;

wherein an amount of probe bound to the test sample higher than an amount of probe bound to a negative control sample is indicative of the presence of *Taenia saginata* eggs in the sample.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 158 base pairs

```
            (B) TYPE: nucleic acid
            (C) STRANDEDNESS: single
            (D) TOPOLOGY: linear (xi) SEQUENCE DESCRIPTION: SEQ ID NO:1:

CAGGCAGGTG CGCCACGTGG CAGGGTGTGA CGTCATGGCA GGCAGCCTGG CCAATGGGCC        60

TGTCGGCGAT CTGGGTCATG TGCCGCAGTC CACACGGCAA AGGACAGCCT CCGAGGCGGT       120

TGCTAGGCAA CTGGCCTCCT CCCCGGGCCC TGGGGATC                              158

(2) INFORMATION FOR SEQ ID NO:2:

(i) SEQUENCE CHARACTERISTICS:
            (A) LENGTH: 967 base pairs
            (B) TYPE: nucleic acid
            (C) STRANDEDNESS: single
            (D) TOPOLOGY: linear (xi) SEQUENCE DESCRIPTION: SEQ ID NO:2:

CAAGCTCGCA CAGAAACACT GGTTTGTAAC CGAGAGATGC GGCTTCAGTG CTATCGTGGA        60

TGCCATGTCC TGGTGTTGTG TATGTGAATA CGGACGCTGT CAAGATCGCC GTGTGTTTCC       120

ATTACGTCCT GTCGATGGAA TAGCCACTTC TTCCTTTTCC ACCTCTTCCT TCTCACCACT       180

CCTGCTATGG GAGAATTGGA CGTTTTTGAA CATCTTTATT ACAATCATAC GGAGGATGTG       240

TGGTGGCGAA ACCGAGACAG TTAAGACAAG GGTATCTCCG AGTCCGCAGA GCGATCACCA       300

ACACGAAATG GCATGCAGTG AGAGCGAAAT CTGCAGTGTG GTGAAGATCA TAAGCGGGTT       360

GGTATGATTT ATACTTTGTT GGGTTTGTGG TCAGGTTTTG TAGGTTTAAG ATTTAGTTTA       420

TTAATTCGTG TTAATTTTTT AGAGCCTTAT TATAATGTGA TTTCTTTGGA TTGTTATAAT       480

TTTTTGATTA CTAATCATGG AATAATAATG ATTTTCTTTT TTTTAATGCC TATTTTAATA       540

GGTGGTTTCG GCAAATATTT AATTCCTTTG GTTGGTGGGT TATCTGATTT GAATTTACCC       600

CGTTTAAATG CTTTAAGTGC ATGGTTATTG ATTCCTTCGA TGGCTTTTCT TTTGGTTAGT       660

ATGTGTTTGG GTGCTGGTAT AGGGTGGACT TTTTATCCGC CTTTGTCGTC ATCATTATTT       720

TCAAGTAGTA ATGGTGTGGA TTTCTTGATG TTTTCGTTGC ATTTGGCGGG TGCGTCTAGA       780

ATTTTTAGTT CTATTAATTT TATTTGTACT TTGTATAGAA TATTTATGAC TAATATATTT       840

TCTCGTACTT CTATAATATT GTGGGCTTAT TTATTTACGT CTATTTTATT ATTAGTTACT       900

CTTCCTGTAT TAGCAGCTGC TATCACTATG CTTTTATTTG ACCGTAAATT TAGTTCTGCG       960

TTTTTTG                                                                967
```